(12) United States Patent
Yan et al.

(10) Patent No.: US 9,963,479 B2
(45) Date of Patent: May 8, 2018

(54) METHOD FOR PREPARING EPIRUBICIN AND INTERMEDIATE THEREOF

(71) Applicant: Zhejiang Hisun Pharmaceutical Co., Ltd., Taizhou (CN)

(72) Inventors: Wei Yan, Taizhou (CN); Wanzeng Tong, Taizhou (CN); Jianping Wang, Taizhou (CN); Weiqiang Yang, Taizhou (CN); Hongguan Qian, Taizhou (CN)

(73) Assignee: Zhejiang Hisun Pharmaceutical Co., Ltd. (CN)

( * ) Notice: Subject to any disclaimer, the term of this patent is extended or adjusted under 35 U.S.C. 154(b) by 70 days.

(21) Appl. No.: 14/900,921

(22) PCT Filed: Jul. 2, 2013

(86) PCT No.: PCT/CN2013/078672
§ 371 (c)(1),
(2) Date: Dec. 22, 2015

(87) PCT Pub. No.: WO2015/000132
PCT Pub. Date: Jan. 8, 2015

(65) Prior Publication Data
US 2016/0137683 A1 May 19, 2016

(51) Int. Cl.
*C07H 15/252* (2006.01)
(52) U.S. Cl.
CPC .................................. *C07H 15/252* (2013.01)
(58) Field of Classification Search
None
See application file for complete search history.

(56) References Cited

U.S. PATENT DOCUMENTS

| 4,345,068 | A | 8/1982 | Suarato et al. |
| 5,874,550 | A | 2/1999 | van der Rijst et al. |
| 5,945,518 | A | 8/1999 | Bigatti et al. |
| 6,416,754 | B1 | 7/2002 | Brown et al. |
| 2002/0182229 | A1* | 12/2002 | Brown ............... A61K 48/0058 424/247.1 |
| 2007/0142309 | A1 | 6/2007 | Zabudkin et al. |

FOREIGN PATENT DOCUMENTS

WO 8906654 A1 7/1989

OTHER PUBLICATIONS

International Search Report for Application No. PCT/CN2013/078672 dated Mar. 6, 2014.

* cited by examiner

*Primary Examiner* — Layla D Berry
(74) *Attorney, Agent, or Firm* — Lerner, David, Littenberg. Krumholz & Mentlik, LLP

(57) ABSTRACT

The present invention provides a method for preparing epirubicin and an intermediate adaptive to the method. The preparation method may include: reacting tert-Butyldimethylsilyl chloride with N-trifluoroacetyl adriamycin to obtain a compound of formula I N-trifluoroacetyl-14-O-tert-Butyldimethylsilyl adriamycin; oxidizing the compound of formula I to obtain a compound of formula II 4'-ketone-N-trifluoroacetyl-14-O-tert-Butyldimethylsilyl adriamycin; reducing the compound of formula II to obtain a compound of formula III N-trifluoroacetyl-14-O-tert-Butyldimethylsilyl epirubicin; and performing deprotection and hydrolysis reactions on the compound of formula III to obtain epirubicin. The method of the present invention needs low cost, fewer reaction steps, provides high yield and high product purity, and avoids serious pollution caused by a bromination reaction in a conventional method.

20 Claims, No Drawings

METHOD FOR PREPARING EPIRUBICIN AND INTERMEDIATE THEREOF

CROSS-REFERENCE TO RELATED APPLICATION

The present application is a national phase entry under 35 U.S.C § 371 of International Application No. PCT/CN2013/078672 filed Jul. 2, 2013, published as International Publication No. WO 2015/000132 A1, the disclosure of which is hereby incorporated herein by reference.

FIELD OF THE INVENTION

The present invention pertains to the field of synthesis of an organic compound, and more particularly, to a method for preparing epirubicin, and an intermediate adaptive to the method.

BACKGROUND OF THE INVENTION

As an isomeride of adriamycin, epirubicin pertains to an antibiotic antineoplastic drug, and has a mechanism of action of directly intercalating between a nuclear DNA base pair to interfere with a process of transcription and prevent an mRNA from forming, thereby inhibiting synthesis of DNA and RNA. In addition, epirubicin also has an inhibiting effect on Topoisomerase-II. As a cell cycle nonspecific agent, epirubicin is effective on multiple transplantation tumors and is widely used clinically.

Among known chemical synthesis methods for preparing epirubicin, a starting material is, for the most part, daunorubicin, for example, a method for preparing epirubicin by using daunorubicin developed by Farmitalia Corporation as a starting material (referring to U.S. Pat. No. 4,345,068 of Suarato et al). The core of the method is as below: oxidizing 4'-hydroxy of daunorubicin to ketone, conducting a stereospecific reduction along with loss of an optical center to obtain epi-daunorubicin by the required conformation, then brominating a segment of 14-CH$_3$—C(O)— of epi-daunorubicin to obtain a segment of 14-CH$_2$Br—C(O)—, and then obtaining HOCH$_2$—C(O)-group by means of a hydrolysis reaction, thereby obtaining epirubicin. In the method for synthesizing epirubicin according to U.S. Pat. No. 5,874,550, it is also used the same starting material-daunorubicin.

Nevertheless, such synthesis processes need multi-step reactions to generate epi-daunorubicin, and then obtain epirubicin by means of bromination and hydrolysis reactions, which need numerous steps, have low yield (a mass yield is about 22-27%), and cause serious pollution by the bromination reaction and larger destruction of the environment. Therefore, it's necessary to further develop a method for preparing epirubicin in order to overcome the foregoing defects in the prior art.

SUMMARY OF THE INVENTION

It is an object of the invention to provide a new method for preparing epirubicin and a new intermediate adaptive to the method. The method is simple in steps, high in yield, friendly to environment, and capable of overcoming the foregoing defects of the prior art.

Specifically speaking:

According to one aspect, the invention provides a first compound for preparing epirubicin (N-trifluoroacetyl-14-O-tert-Butyldimethylsilyl adriamycin, with a structure as below):

A compound of formula I:

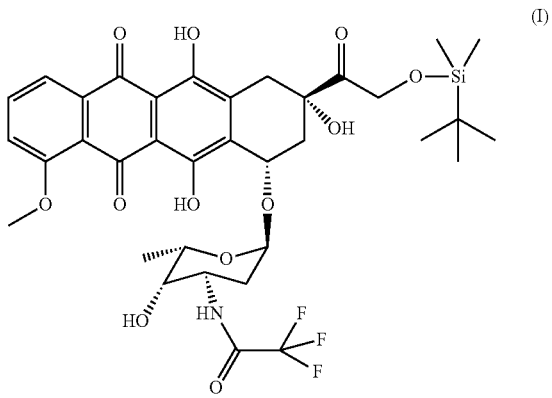

Further, the invention also provides a method for preparing a compound of formula I, and the method includes: using tert-Butyldimethylsilyl chloride as a protective agent to react with N-trifluoroacetyl adriamycin to obtain the compound of formula I whose 14-position hydroxy group is protected. The use of the highly specific protective agent may selectively protect 14-position hydroxy group of N-trifluoroacetyl adriamycin, and obtain a target product at a high conversion rate.

The temperature of the foregoing protective reaction is preferably 0-50° C., and more preferably 20-30° C. In the reaction, it is preferably used an alkaline deacid reagent, for example, an organic base such as imidazole (1,3-diazabicyclo-2,4-cyclopentadiene), pyridine or DMAP (4-dimethylaminopyridine) or the like; preferably the reaction is conducted in an aprotic solvent, for example, DMF (N,N-dimethylformamide), DMAC (N,N-dimethylacetamide), DMSO (dimethyl sulfoxide) and acetonitrile, etc. Preferably, a molecular sieve is used to remove moisture in the reaction.

The N-trifluoroacetyl adriamycin may be purchased commercially, or obtained by means of a similar method known in the art, for example, the N-trifluoroacetyl adriamycin may be obtained from adriamycin through acylation by means of a method similar to the method as described in US Patent US2007142309, and the concrete reaction steps are as below:

In a dry and water-immiscible aprotic solvent, mixing and reacting an acylating agent, preferably TFAA (trifluoroacetic anhydride), with adriamycin, then adding alkaline aqueous solution into the system, and further mildly hydrolyzing acylamino-ester obtained into N-trifluoroacetyl adriamycin in the alkaline aqueous solution-organic solution biphasic system of acylamino-ester.

The aprotic solvent is preferably DCM (dichloromethane) or chloroform, and further preferably DCM. The alkaline aqueous solution may be ammonia water or sodium bicarbonate aqueous solution, preferably sodium bicarbonate aqueous solution.

According to another aspect, the invention provides a second compound for preparing epirubicin (4'-ketone-N-trifluoroacetyl-14-O-tert-Butyldimethylsilyl adriamycin, with a structure as below):

A compound of formula II:

(II)

Further, the invention provides a method for preparing the compound of formula II, which is obtained by oxidizing the compound of formula I, and the method includes:

In an aprotic solvent, activating the compound of formula I by using DMSO (dimethylsulfoxide) activated by an acylating agent, and then processing the compound of formula I by using 1,5-diazabicyclo[4.3.0]non-5-ene (DBN), thereby obtaining the compound of formula II.

The temperature of the oxidizing reaction is between −80° C. and −20° C., preferably between −70° C. and −40° C., and further preferably between −65° C. and −60° C.

The acylating agent is preferably TFAI (trifluoroacetyl imidazole), trifluoroacetic anhydride or $SOCl_2$.

The aprotic solvent includes but is not limited to one or more of: DMAA (N,N-dimethylacrylamide), DMAP (4-dimethylaminopyridine), HMPA (hexamethylphosphoramide), halogenated hydrocarbon (for example, DCM, chloroform or the like) of $C_1$-$C_4$ and $C_1$-$C_4$-alkyl-substituted aromatic hydrocarbon (for example, benzene, methylbenzene or the like), preferably DCM.

According to the method of the invention, a total mass yield of the reaction may be above 90%.

According to another aspect, the invention further provides a third compound for preparing epirubicin (N-trifluoroacetyl-14-O-tert-Butyldimethylsilyl epirubicin, with a structure as below):

A compound of formula III:

(III)

Further, the invention also provides a method for preparing the compound of formula III, and the method includes:

Reducing the compound of formula II in the presence of a reductant.

The reductant is borohydride of an alkali metal or a derivative thereof, which may be expressed by a general formula $MHBL_3$, where M is selected from Li, Na or K; L is selected from H, AlkO, AlkCOO or ArCOO, where Alk is a straight-chain alkyl group of $C_1$-$C_4$, preferably Me, Et or n-Pr; Ar is a phenyl group or an alkyl-substituted phenyl group, the alkyl group is preferably selected from a $C_1$-$C_4$ straight-chain alkyl group.

Preferably the reductant is sodium borohydride.

According to the method of the invention, a total mass yield of the reaction may be above 90%.

According to another aspect, the invention further provides a method for preparing epirubicin, and the method includes a step of performing a deprotection reaction on the compound of formula III to generate N-trifluoroacetyl epirubicin, and then converting N-trifluoroacetyl epirubicin into epirubicin.

The foregoing deprotection reaction may be conducted, in the presence of a deprotective agent, in an aprotic solvent, for example, DCM, acetonitrile or the like, 14-position hydroxy protecting group $(CH_3)_3CSi(CH_3)_2$— of the compound of formula III is removed, and N-trifluoroacetyl epirubicin is obtained.

The deprotective agent is selected from tetrabutylammonium fluoride, hydrofluoric acid or potassium fluoride, preferably tetrabutylammonium fluoride.

Preferably, DCM is used as a solvent in the deprotection reaction.

Preferably, the deprotection reaction is conducted at room temperature.

In the method for converting N-trifluoroacetyl epirubicin into epirubicin, it may be used a method in which 14-OH is protected and then trifluoroacetyl and a 14-OH protecting group are removed successively, just as described in U.S. Pat. No. 5,874,550; or epirubicin may also be obtained by using a one-step hydrolysis method.

In the hydrolysis method, a hydrolysis reaction is conducted in aqueous alkaline solution having a pH of 10-13, preferably the hydrolysis temperature is between −10° C. and 40° C., and further preferably between 0° C. and 20° C., thereby obtaining epirubicin by hydrolyzing N-trifluoroacetyl epirubicin.

Optionally, the method further includes a step of salifying epirubicin obtained by means of hydrolysis by methods well known in the art, and the salt is preferably hydrochloride.

In a preferred embodiment, the method for preparing epirubicin further includes a step of obtaining the compound of formula III from the compound of formula II, and the step includes reducing the compound of formula II in the presence of a reductant.

The reductant is borohydride of an alkali metal or a derivative thereof, which may be expressed by a general formula $MHBL_3$, where M is selected from Li, Na or K; L is selected from H, AlkO, AlkCOO or ArCOO, where Alk is a straight-chain alkyl group of $C_1$-$C_4$, preferably Me, Et or n-Pr; Ar is a phenyl group or an alkyl-substituted phenyl group, the alkyl group is preferably a $C_1$-$C_4$ straight-chain alkyl group; and the reductant is preferably sodium borohydride.

The reaction temperature is between −70° C. and 0° C., preferably between −70° C. and −40° C., and further preferably between −70° C. and −65° C.

Preferably, a product obtained in the step is not purified and directly used in a subsequent reaction.

In a further preferred embodiment, the method further includes a step of preparing the compound of formula II by oxidizing the compound of formula I, and the step includes: in an aprotic solvent, activating the compound of formula I by using DMSO (dimethyl sulfoxide) activated by an acylating agent, and then processing the compound of formula I by using 1,5-diazabicyclo[4.3.0]non-5-ene (DBN), thereby obtaining the compound of formula II.

The temperature of the oxidizing reaction is between −80° C. and −20° C., preferably between −70° C. and −40° C., and further preferably between −65° C. and −60° C.

The acylating agent is preferably TFAI (trifluoroacetyl imidazole), trifluoroacetic anhydride or $SOCl_2$.

The aprotic solvent includes but is not limited to one or more of: DMAA (N,N-dimethylacrylamide), DMAP (4-dimethylaminopyridine), HMPA (hexamethylphosphoramide), halogenated hydrocarbon (for example, DCM, chloroform or the like) and aromatic hydrocarbon (for example, benzene, methylbenzene or the like), preferably DCM.

Preferably, a product obtained in the step is not purified and directly used in a subsequent reaction.

In a still further preferred embodiment, the preparation method further includes a step of preparing the compound of formula I from N-trifluoroacetyl adriamycin, and the method includes: using tert-Butyldimethylsilyl chloride as a protective agent to react with N-trifluoroacetyl adriamycin, thereby obtaining the compound of formula I whose 14-position hydroxy group is protected.

The temperature of the foregoing protective reaction is 0-50° C., and preferably 20-30° C. It is preferably used an alkaline deacid reagent, for example, an organic base such as imidazole (1,3-diazabicyclo-2,4-cyclopentadiene), pyridine or DMAP (4-dimethylaminopyridine) or the like; preferably the reaction is conducted in an aprotic solvent, for example, DMF (N,N-dimethylformamide), DMAC (N,N-dimethylacetamide), DMSO (dimethyl sulfoxide) and acetonitrile, etc.

Preferably, a molecular sieve is used to remove moisture in the reaction.

The N-trifluoroacetyl adriamycin may be purchased commercially, or obtained by means of a similar method known in the art.

Preferably, a product obtained in the step is not purified and directly used in a subsequent reaction.

In a still further preferred embodiment, the preparation method further includes a step of preparing N-trifluoroacetyl adriamycin from adriamycin, and the step includes:

In a dry and water-immiscible aprotic solvent, mixing and reacting an acylating agent, preferably TFAA (trifluoroacetic anhydride), with adriamycin, then adding alkaline aqueous solution into the system, and further mildly hydrolyzing acylamino-ester obtained into N-trifluoroacetyl adriamycin in the alkaline aqueous solution-organic solution biphasic system of acylamino-ester.

The aprotic solvent is preferably DCM (dichloromethane) or chloroform, and further preferably DCM. The alkaline aqueous solution may be ammonia water or sodium bicarbonate aqueous solution, preferably sodium bicarbonate aqueous solution.

Preferably, a product obtained in the step is not purified and directly used in a subsequent reaction.

The invention has the following beneficial effects.

It is provided a new method for preparing epirubicin, and an intermediate compound adaptive to the method. In the method, easily-obtained adriamycin is used as a raw material, reaction steps are fewer, various reaction products may be used in a subsequent reaction without purification, the reaction yield and the product purity are high. Furthermore, the method avoids serious pollution caused by a bromination reaction in a conventional method, and effectively reduces economic cost and environmental cost.

DETAILED DESCRIPTION OF THE EMBODIMENTS

The following embodiments may facilitate further understanding the invention, but is not intended to limit the content of the invention.

The raw material adriamycin and reagents in the embodiments of the invention can be purchased from the market.

Embodiment I: Synthesis of N-trifluoroacetyl adriamycin (a) suspending 5 g adriamycin in 200 ml DCM, cooling it to 0° C., stirring and slowly dropwise adding mixed liquor of 8 ml DCM and 15 ml trifluoroacetic anhydride within 30 min, and then stirring for reaction for 30 min;

(b) at 0° C., adding methanol into the mixed liquor obtained, stirring for 30 min, and heating up to room temperature;

(c) adding 200 ml saturated sodium bicarbonate solution into the mixed liquor, stirring for 10 hours at room temperature for a hydrolysis reaction;

(d) after completing hydrolysis (according to an HPLC detection), separating an organic layer, dehydrating an organic phase, decompressing and concentrating until it is dried, obtaining an oily substance of 6 g by weighting, an HPLC measurement showing that a chromatographic purity of N-trifluoroacetyl adriamycin is 93%, which may be wholly and directly used in reactions of the following embodiments (no need of further purification, also applicable to the following embodiments).

Embodiment II: Preparation of N-trifluoroacetyl-14-O-tert-Butyldimethylsilyl adriamycin (the Compound of Formula I)

(a) adding 50 ml DMF to dissolve the condensate obtained from Embodiment I, adding 5 g dried molecular sieve and 1 g imidazole, stirring for dissolution;

(b) adding, at 25° C., mixed solution of 1.5 g tert-Butyldimethylsilyl chloride and 10 ml DMF into the mixture obtained for reaction for 6 hours;

(c) adding 200 ml DCM and 100 ml HCl aqueous solution having a pH of 2.0 into the reaction liquid, stirring and conducting a liquid separation; using 100 ml water to rinse an organic phase, and separating an organic layer, after dehydration, decompressing and concentrating the organic phase until it is dried, obtaining 6 g solid, an HPLC measurement showing that a chromatographic purity of N-trifluoroacetyl-14-O-tert-Butyldimethylsilyl adriamycin is 91%, which is wholly and directly used in reactions of the following Embodiment III.

$^1$H-NMR (400 MHZ, DMSO):

0.05 (t, 7H); 0.88 (s, 9H); 1.12 (d, 3H); 1.46 (dd, 1H); 2.05-2.11 (dd, 2H); 2.18 (d, 1H); 2.89 (t, 1H); 3.01-3.06 (d, 1H); 3.51 (d, 1H); 3.99 (s, 4H); 4.21 (d, 1H); 4.84 (d, 2H); 5.0 (d, 1H); 5.25 (s, 1H); 5.49 (s, 1H); 7.65 (t, 1H); 7.92 (d, 2H); 9.10 (d, 1H); 13.28 (s, 1H); 14.05 (s, 1H).

Embodiment III: Preparation of 4'-ketone-N-trifluoroacetyl-14-O-tert-Butyldimethylsilyl adriamycin (the Compound of Formula II)

(a) mixing 100 ml DCM and 5 ml DMSO while stirring, cooling to −60° C., then adding mixed liquor of 5 ml trifluoroacetic anhydride and 10 ml DCM, and stirring for 15 min;

(b) mixing 6.0 g N-trifluoroacetyl-14-O-tert-Butyldimethylsilyl adriamycin obtained from Embodiment II with 50 ml DCM, then dropwise adding it, within 30 min, into the mixed liquor obtained in Step (a) at a temperature controlled between −65° C. and −60° C., after which, continuing reaction for 45 min at the temperature between −65° C. and −60° C.;

(c) adding 5 ml DBN solution, and continuing reaction for 10 min at the temperature between −65° C. and −60° C.;

(d) adding 3 ml glacial acetic acid to neutralize the reaction liquid, then adding 100 ml water, stirring and conducting a liquid separation, rinsing it once by 100 ml water, separating an organic phase, then dehydrating;

(e) after decompressing and concentrating, obtaining 5.7 g oily substance, an HPLC measurement showing that a chromatographic purity of 4'-ketone-N-trifluoroacetyl-14-O-tert-Butyldimethylsilyl adriamycin is 85%, which is directly used in reactions of the following Embodiments IV.

$^1$H-NMR (400 MHZ, DMF):

0.05 (t, 6H); 0.82 (s, 9H); 1.14 (d, 3H); 1.56 (dd, 1H); 2.10-2.18 (m, 2H); 2.28-2.32 (d, 1H); 2.93 (d, 1H), 3.06-3.11 (d, 1H); 3.58 (d, 1H); 4.0 (s, 3H); 4.25-4.3 (dd, 1H); 4.90 (s, 2H); 5.05 (d, 1H); 5.30 (d, 1H); 5.56 (s, 1H); 7.61 (d, 1H); 7.84 (m, 2H); 9.03 (d, 1H) 13.20 (s, 1H); 14.15 (s, 1H).

Embodiment IV: Preparation of N-trifluoroacetyl-14-O-tert-Butyldimethylsilyl epirubicin (the Compound of Formula III)

(a) stirring and dissolving 5.7 g ketone product obtained from Embodiment III with 80 ml absolute methanol and 40 ml DCM, then cooling to between −70° C. and −65° C.;

(b) after dissolving 0.1 g sodium borohydride with 35 ml absolute ethyl alcohol, adding it into the reaction liquid within 5 min at a temperature controlled between −70° C. and −65° C., then stirring for reaction for 30 min;

(c) adding mixed liquor of 150 ml DCM and 100 ml hydrochloric acid solution having a pH of 3 into the reaction liquid, stirring, conducting a liquid separation, rinsing an organic phase obtained twice by 150 ml pure water, then dehydrating and drying the organic phase;

(d) after concentrating, obtaining 5.4 g oily substance, an HPLC measurement showing that a chromatographic purity of N-trifluoroacetyl-14-O-tert-Butyldimethylsilyl epirubicin is 75%, which is directly used in reactions of the following Embodiments V.

$^1$H-NMR (400 MHZ, DMSO):

0.04 (t, 7H); 0.88 (s, 9H); 1.13 (d, 3H); 1.47 (dd, 1H); 2.06-2.13 (dd, 2H); 2.19 (d, 1H); 2.92 (t, 1H); 3.01-3.06 (d, 1H); 3.52 (d, 1H); 3.99 (s, 4H); 4.23 (d, 1H); 4.84 (d, 2H); 4.94 (s, 1H); 5.25 (s, 1H); 5.49 (s, 1H); 7.65 (t, 1H); 7.92 (d, 2H); 9.10 (d, 1H); 13.28 (s, 1H); 14.05 (s, 1H).

Embodiment V: Preparation of N-trifluoroacetyl epirubicin (a) stirring and dissolving 5.4 g N-trifluoroacetyl-14-O-tert-Butyldimethylsilyl epirubicin with 150 ml DCM, then adding 5 g tetrabutylammonium fluoride for reaction for 4 hours at room temperature, after complete reaction, adding 100 ml water into the reaction liquid, stirring, conducting a liquid separation, and dehydrating;

(b) obtaining 5.3 g solid after concentration, then purifying the obtained solid by means of silica gel, and collecting liquid whose HPLC chromatographic purity is greater than 98.5%;

(c) after the collected liquid is concentrated and dried, obtaining 3.0 g solid, an HPLC measurement showing that a chromatographic purity of N-trifluoroacetyl epirubicin is 99%, which is directly used in reactions of the following Embodiments VI.

Embodiments VI: Preparation of Epirubicin Hydrochloride (a) preparing 120 ml NaOH aqueous solution having a pH of 13, cooling it to 0° C., then adding 3.0 g N-trifluoroacetyl epirubicin having been dissolved in 30 ml methanol, stirring for reaction for 1 hour at 0° C., after a neutralization by means of hydrochloric acid solution until pH is equal to 4, obtaining a feed liquor having a small volume by means of concentration, then adding the feed liquor into 150 ml acetone, stirring for 2 hours at room temperature, then filtering, and obtaining 2.0 g solid epirubicin hydrochloride (having a chromatographic purity of 98.5%).

Measured in adriamycin, a total mass yield of epirubicin prepared from adriamycin according to Embodiments I-VI is 2.0/5*100%=40%.

$^1$H-NMR (400 MHZ, H$_2$O):

1.4 (t, 3H); 1.95-2.04 (m, 2H); 2.25-2.35 (dd, 2H); 2.6 (d, 1H); 2.9 (d, 1H); 3.4-3.51 (m, 2H); 3.87 (s, 3H); 3.99-4.06 (m, 1H); 4.76 (s, 1H); 4.8-4.91 (dd, 2H); 5.4 (s, 1H); 7.3 (m, 2H); 7.6 (t, 1H).

What is claimed is:

1. A method for preparing epirubicin, comprising the following steps:

reacting a compound of formula III

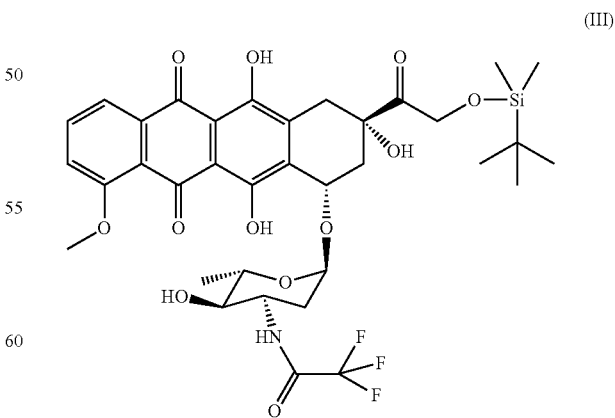

(III)

with a deprotective agent for dehydroxylation of 14-position hydroxy protecting group (CH$_3$)$_3$CSi(CH$_3$)$_2$— of the compound, to obtain N-trifluoroacetyl epirubicin, converting the N-trifluoroacetyl epirubicin into epirubicin; wherein, the deprotective agent is selected from tetrabutylammonium fluoride, hydrofluoric acid or potassium fluoride; and wherein a solvent of the deprotective reaction is dichloromethane or acetonitrile.

2. The method for preparing epirubicin according to claim 1, further comprising the following steps:
reducing a compound of formula II,

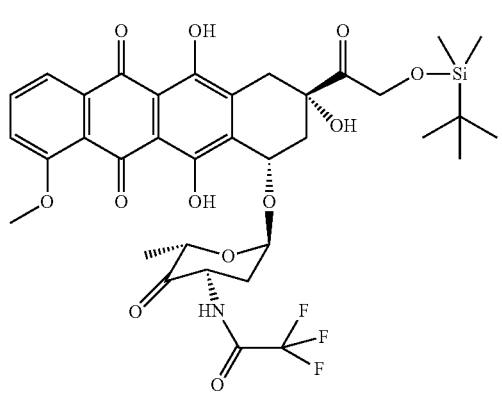

in the presence of a reductant to obtain the compound of formula III:

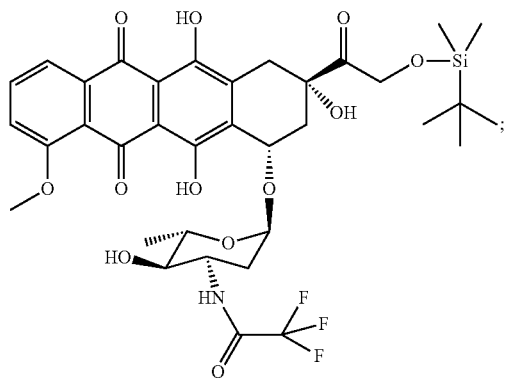

wherein the reductant is borohydride of an alkali metal or a derivative thereof, with a general formula $MHBL_3$, wherein M=Li, Na or K;
L=H, AlkO, AlkCOO or ArCOO, wherein Alk is a straight-chain alkyl group of $C_1$-$C_4$; Ar is a phenyl group or an alkyl-substituted phenyl group, the alkyl-substituted phenyl group is selected from a $C_1$-$C_4$ straight-chain-alkyl-substituted phenyl group.

3. The method for preparing epirubicin according to claim 2, further comprising the following steps:

reacting, in an aprotic solvent, a compound of formula I

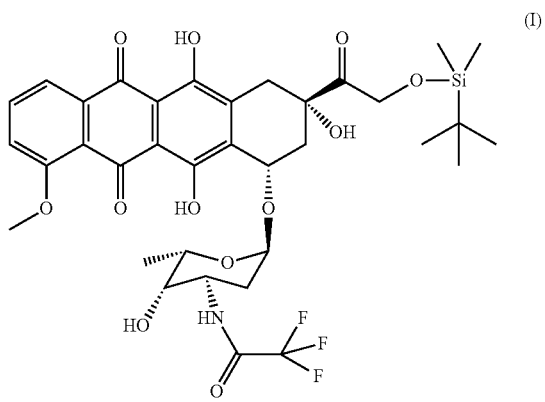

with dimethylsulfoxide activated by an acylating agent, then processing by using 1,5-diazabicyclo[4.3.0]non-5-ene, thereby obtaining the compound of formula II;

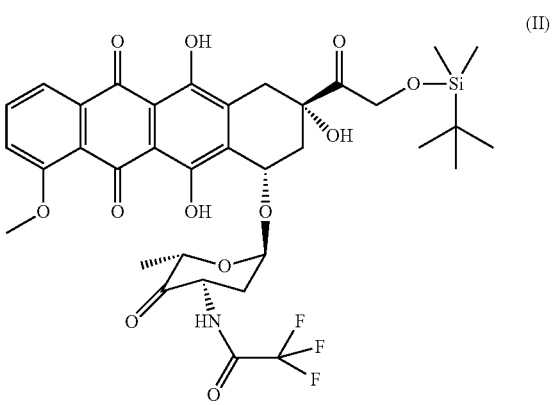

wherein the acylating agent is selected from trifluoroacetyl imidazole, trifluoroacetic anhydride or $SOCl_2$;
wherein, the temperature of the foregoing reaction is controlled between −80° C. and −20° C.

4. The method for preparing epirubicin according to claim 3, further comprising the following steps:
using tert-Butyldimethylsilyl chloride as a protective agent to react with N-trifluoroacetyl adriamycin to obtain the compound of formula I whose 14-position hydroxy group is protected;
wherein, the reaction is conducted in the presence of a deacid reagent, wherein the deacid reagent is selected from imidazole, pyridine or 4-dimethylamino-pyridine;
wherein, the reaction temperature is 0-50° C.; and
wherein, a reaction solvent is selected from N,N-dimethyl formamide, N,N-dimethylacetamide, dimethyl sulfoxide or acetonitrile.

5. The method for preparing epirubicin according to any one of claim 1, characterized in that conversion of the N-trifluoroacetyl epirubicin into epirubicin is conducted by way of hydrolysis; wherein the hydrolysis reaction is conducted in alkaline aqueous solution having a pH of 10-13; wherein the hydrolysis temperature is between −10° C. and 40° C.

6. A compound of formula I

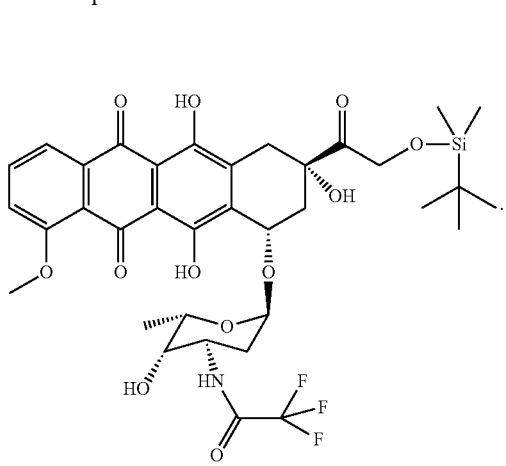

7. A method for preparing the compound of formula I according to claim 6, characterized in that the method comprises: using tert-Butyldimethylsilyl chloride to protect 14-position hydroxy group of N-trifluoroacetyl adriamycin, to obtain the compound of formula I.

8. The method for preparing the compound of formula I according to claim 7, characterized in that the reaction is conducted in the presence of a deacid reagent; wherein the deacid reagent is selected from imidazole, pyridine or 4-di-methylamino-pyridine; wherein a reaction temperature is 0-50° C., and wherein a reaction solvent is selected from N,N-dimethyl formamide, N,N-dimethylacetamide, dimethyl sulfoxide or acetonitrile.

9. The method for preparing the compound of formula I according to claim 8, characterized in that the N-trifluoro-acetyl adriamycin is obtained by acylating adriamycin;
wherein an acylating agent used is trifluoroacetic anhydride, and a solvent used in an acylation reaction is dichloromethane or chloroform.

10. A compound of formula II:

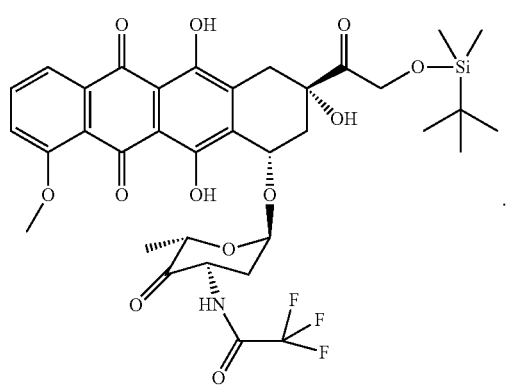

11. A method for preparing the compound of formula II of claim 10, characterized in that the method comprises: reacting, in an aprotic solvent, a compound of formula I

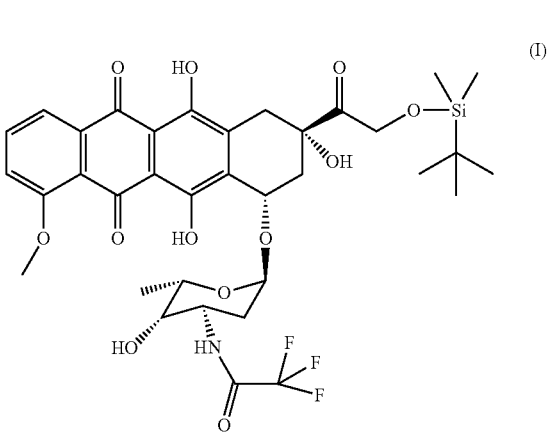

with dimethylsulfoxide activated by an acylating agent, and then processing by using 1,5-diazabicyclo[4.3.0] non-5-ene, thereby obtaining the compound of formula II;
wherein the acylating agent is selected from trifluoro-acetyl imidazole, trifluoroacetic anhydride or $SOCl_2$; and
wherein the reaction temperature is between −80° C. and −20° C.

12. The method for preparing the compound of formula II of claim 11, characterized in that the aprotic solvent is selected from one or more of N,N-dimethylacrylamide, 4-dimethylaminopyridine, hexamethylphosphoramide, halogenated hydrocarbon of $C_1$-$C_4$ and $C_1$-$C_4$-alkyl-substituted aromatic hydrocarbon.

13. A method for preparing compound of formula III, characterized in that the method comprises: reducing the compound of formula II of claim 11 to obtain the compound of formula III:

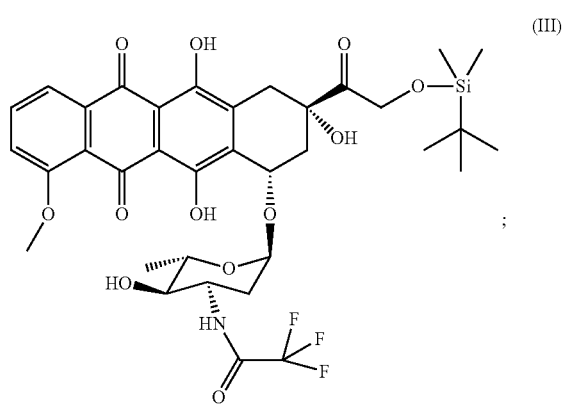

wherein a reductant used is sodium borohydride.

14. The method for preparing epirubicin according to claim 1, characterized in that the deprotective agent is selected from tetrabutylammonium fluoride.

15. The method for preparing epirubicin according to claim 2, characterized in that the Alk is Me, Et or n-Pr.

16. The method for preparing epirubicin according to claim 3, characterized in that the temperature of the foregoing reaction is controlled between −70° C. and −40° C.

17. The method for preparing epirubicin according to claim 5, characterized in that the hydrolysis temperature is between 0° C. and 20° C.

18. The method for preparing epirubicin according to claim 8, characterized in that the reaction temperature is 20-30° C.

19. The method for preparing the compound of formula II of claim 11, characterized in that the reaction temperature is between −70° C. and −40° C.

20. The method for preparing the compound of formula II of claim 11, characterized in that the aprotic solvent is dichloromethane.

* * * * *